United States Patent [19]

Messina et al.

[11] Patent Number: 5,017,721

[45] Date of Patent: May 21, 1991

[54] PROCESS FOR THE PREPARATION OF OXALYL- AND OXAMYL-HYDRAZIDES

[75] Inventors: Giuseppe Messina, Alghero; Loreno Lorenzoni, Porto Torres; Paolo Calaresu, Sassari; Giovanni M. Sechi, Ozieri, all of Italy

[73] Assignee: Enichim ANIC S.p.A., Palermo, Italy

[21] Appl. No.: 341,749

[22] Filed: Apr. 21, 1989

[30] Foreign Application Priority Data

Apr. 21, 1988 [IT] Italy .............................. 20276 A/88

[51] Int. Cl.$^5$ ............... C07C 741/02; C07D 295/023; C07D 279/12; C07D 279/06
[52] U.S. Cl. ....................................... 564/151; 544/3; 544/54; 544/58.1; 544/63; 544/88; 544/164; 544/224; 544/322; 544/382; 546/244; 548/195; 548/214; 548/215; 548/240; 548/356; 548/300; 548/557; 558/422; 558/423; 558/431; 558/445; 560/34; 560/125; 560/169; 562/439; 562/507; 562/560; 564/148; 564/149; 564/150
[58] Field of Search ............... 564/149, 151, 148, 150; 558/393, 412, 418, 419, 438, 439; 544/3, 54, 58.1, 63, 88, 164, 224, 322, 382

[56] References Cited

U.S. PATENT DOCUMENTS 3,948,931  4/1976  Allgeier et al. .................. 260/308 R
3,960,946  6/1976  Dewitt et al. .................... 260/561 H

FOREIGN PATENT DOCUMENTS 0661966  4/1963  Canada .

Primary Examiner—Richard L. Raymond
Assistant Examiner—Peter G. O'Sullivan
Attorney, Agent, or Firm—Oblon, Spivak, McClelland, Maier & Neustadt

[57] ABSTRACT

A new process for preparing oxalyl- and oxamyl-hydrazides which comprises contacting oxamide or diacetyloxamide with the corresponding hydrazine derivative of formula $R_1R_2N-NHR_3$

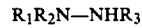

wherein $R_1$ represents a hydrogen atom or an optionally substituted alkyl, cycloalkyl, aryl, or aryl-alkyl group, $R_2$ is a hydrogen atom or an optionally substituted alkyl group, or $R_1$ and $R_2$ taken together with the adjacent nitrogen atom represent a saturated heterocyclic ring, and $R_3$ is a hydrogen atom or an optionally substituted alkyl group.

8 Claims, No Drawings

PROCESS FOR THE PREPARATION OF OXALYL- AND OXAMYL-HYDRAZIDES

The present invention refers to a new process for the preparation of oxalyl- and oxamyl-hydrazides of general formula (I)

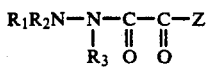  (I)

wherein
- R₁ represents a hydrogen atom or an optionally substituted alkyl, cycloalkyl, phenyl, or phenyl-alkyl group,
- R₂ designates a hydrogen atom or an optionally substituted alkyl group, or, R₁ and R₂ taken together with the adjacent nitrogen atom represent a saturated heterocyclic ring,
- R₃ is a hydrogen atom or an optionally substituted alkyl group,
- Z is —NR₃—NR₁R₂, wherein R₁, R₂, and R₃ are as defined above, or —NH₂;

which comprises contacting a compound, selected from oxamide or its diacetyl derivative, of formula (II)

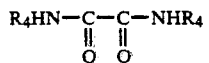  (II)

wherein
R₄ is a hydrogen atom or an acetyl group, with a hydrazine derivative of formula (III)

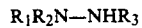  (III)

wherein
R₁, R₂, and R₃ are as defined above.

For the purposes of the present invention, the term "alkyl", both when it is used to identify a radical per se and when it is employed to define part of a combined group, such as the alkyl moiety in the "phenyl-alkyl" group, designates a straight or branched alkyl radical, generally containing from 1 to 12 carbon atoms, which may be unsubstituted or contain one or more substituents. Substituents which do not negatively interfere with the reaction course and can therefore be present are for instance dialkylamino, hydroxy, alkoxy, carboxy, carbalkoxy, formyl, oxo, mercapto, alkylthio, cyano, nitro, halogen, etc..

The term "cycloalkyl" designates a saturated 5- to 12-membered cycloaliphatic ring.

Substituents which may be present on the cycloalkyl ring or on the phenyl ring, when R₁ represents a substituted phenyl or phenyl-(C₁-C₄)alkyl group, are those listed above, as well as alkyl, halo-alkyl, hydroxy-alkyl, and the like groups.

Finally the term "saturated heterocyclic ring", designates a saturated 5-, or 6-membered heterocyclic ring which may contain an additional heteroatom selected from —O—, —S—, and —N(H,Alkyl)—, and be alkyl-substituted.

The oxalic acid dihydrazide ((I): Z=—NR₃—NR₁R₂, wherein R₁, R₂, and R₃=H) is a widely known chemical compound with several industrial utilities. In particular, as an example, it may be employed as starting compound for the preparation of bis- and poly-oxadiazoles useful as fluorescent bleaching agents for polyesters (see Chemical Abstracts Vol. 79:66865y. 101:31096 u; 103:72608 x; 107:134264 a), as a stabilizer or a polymer additive (Chem. Abst. 76:154811 w; 79:79785 x; 105:80060 u), in the preparation of hydrazine copolymers (Chem. Abst. 91:6252 j; 98:108620 q), as polycondensation catalyst (Chem. Abst. 89:198046 y), as a reagent in the determination of serum copper (Chem. Abst. 75:17222 v) or of serum selenium (Chem. Abst. 98:10839 t), or as a ligand in particular bi-metallic complexes with antifungal activity (Chem. Abst. 103:226232 j). The compound of formula (I) wherein Z is an —NH₂ group, and R₁, R₂, and R₃ are hydrogen, also is a known compound employed as starting material in the preparation of oxamic acid alkoxy-alkylidenhydrazides (see Japanese patent application publication no. 210056/84 (Chem. Abst. 102:166337 q)). The methods known in literature and actually employed for the preparation of these compounds involve the introduction of the hydrazino moiety on one or both carbonyl groups, by exchange with an alkoxy group. In order to prepare oxalic acid dihydrazide, the starting compound is therefore a diester, and typically oxalic acid diethyl ester, while for the preparation of the oxamyl-hydrazide, the starting compound is an oxamic acid ester. Said reactants are however fairly expensive, cannot be managed easily, and furthermore they are prepared from oxalic acid or oxalyl chloride, which are highly toxic reactants.

It has now been found that it is possible to prepare these compounds and other N- or N'-substituted derivatives by a generally applicable reaction which comprises reacting oxamide or diacetyloxamide, with a hydrazine derivative of formula (III)

  (III)

wherein R₁, R₂, and R₃ are as defined above.

In actual practice, the reaction may be carried out by simply adding the starting oxamide of formula (II) to a molar excess of the hydrazine derivative (III) with respect to the stoichiometric amount, optionally in the presence of water or an inert, polar, organic solvent.

Preferred organic solvents are polar organic solvents, inert toward the reactants employed, which are capable of dissolving both the starting hydrazine derivative and the reaction product of formula (I), so that any unreacted oxamide (II) may be easily removed by filtration.

The reaction is generally carried out at a temperature of from room temperature to 100° C. and, preferably, at a temperature of from 30 to 80° C. At the end of the reaction, which is generally complete in a few hours, the desired product is recovered according to conventional methods which depend on the particular hydrazine derivative of formula (III) which has been employed.

When according to a preferred embodiment of the present invention, the process is used for the preparation of oxalyl-hydrazide (Z=—NR₃—NR₁R₂, R₁=R₂=R₃=H), the reaction is preferably carried out with hydrazine hydrate, or possibly an aqueous solution of hydrazine hydrate, using the excess of said reactant as the reaction medium. In this case recovery of the desired product involves recovery of the precipitated product by filtration and washing of this precipitate with a strongly polar organic solvent. If desired, said product may be purified by chromatographic techniques.

The following examples which describe the process of the present invention in some representative embodiments thereof, must not be interpreted as a limitation to the scopes of the present invention.

EXAMPLE 1

Preparation of oxalic acid dihydrazide

99% Hydrazine hydrate (50 ml, 51.5 g, 1.03 mol) is charged into a 100-ml, three-necked flask equipped with a thermometer, a reflux condenser, an inlet tube for nitrogen, and a magnetic stirrer. The temperature is brought to 50° C., and oxamide (10 g, 0.11 mol) is gradually stirred in. Ammonia which forms is removed as soon as it forms by a slow nitrogen stream. After two hours, the mixture is cooled to 25° C. and filtered under vacuum washing the precipitate on filter with methyl alcohol. The precipitate is then dried in the oven at 100° C., yielding the compound of the title (12.5 g, 0.11 mol, 93.2% yield) as a highly pure product.

The FTIR spectrum of the thus obtained compound (absorption maxima at 3280, 3180, 1660, and 1620 cm$^{-1}$) overlaps with that of an authentic sample.

EXAMPLE 2

Preparation of oxalic acid dihydrazide

99% Hydrazine hydrate (61.8 g, 1.23 mol) is charged into a 100-ml, three-necked flask equipped with a thermometer, a reflux condenser, an inlet tube for nitrogen, and a magnetic stirrer. The temperature is brought to 30° C., and oxamide (10 g, 0.11 mol) is gradually stirred in. Ammonia which forms during the reaction, is removed as soon as it forms by a nitrogen stream. After two hours, the mixture is cooled to 20° C. and filtered under vacuum washing the precipitate on filter with methyl alcohol. The precipitate is then dried in the oven at 100° C., yielding the compound of the title (13.1 g, 97.8% yield) with m.p. 244–6° C.

Elemental analysis: Calculated for $C_2H_6N_4O_2$: C 20.34%; H 5.08%; N 47.46%. Found: C 20.28%; H 5.15%; N 47.01%.

EXAMPLE 3

Preparation of oxalic acid dihydrazide

98% Hydrazine hydrate (61.8g, 1.23 mol) is charged into a multi-necked flask equipped with a thermometer, a reflux condenser, an inlet tube for nitrogen, and a magnetic stirrer. Under stirring N,N'-diacetyloxamide (20 g, 0.116 mol) is added portionwise, while keeping the temperature of the reaction mixture at 25° C. The reaction mixture is then heated to 75° C. and allow to react for about 90 minutes. The mixture is then cooled to room temperature, filtered under vacuum and the precipitate on filter is washed with methyl alcohol. The compound of the title is thus obtained (12.4 g, 0.105 mol, 90.5% yield) with m.p. 245.7° C.

Elemental analysis: Calculated for $C_2H_6N_4O_2$: C 20.34%; H 5.08%; N 47.46% Found: C 20.30%; H 5.10%; N 47.40%

EXAMPLE 4

Preparation of oxamyl-hydrazide

A dispersion of N,N'-diacetyloxamide (10 g, 0.058 mol) in anhydrous ethyl alcohol (40 ml) is charged into a 100-ml, four-necked flask equipped with a thermometer, a reflux condenser, a dropping funnel, an inlet tube for nitrogen, and a magnetic stirrer. 98% Hydrazine monohydrate (20 ml, 0.407 mol) is added thereto. The temperature rises from the room value to 45° C. When the addition is terminated the temperature is brought to 75° C. and the reaction is allowed to proceed for further two hours. The mixture is then cooled, filtered under vacuum and the precipitate on filter is washed with acetone. Oxamic acid hydrazide is thus obtained (5.4 g, 90% yield) with m.p. 212–5° C. (Lit. 218° C. with dec.). The structure of the thus obtained product has been confirmed by comparing its I.R. spectrum with that of an authentic sample.

We claim:

1. A process for the preparation of oxamyl-hydrazide of formula (I)

$$R_1R_2N-\underset{\underset{R_3}{|}}{N}-\underset{\underset{O}{\|}}{C}-\underset{\underset{O}{\|}}{C}-Z \qquad (I)$$

wherein
$R_1$ represents a hydrogen atom or an optionally substituted alkyl, cycloalkyl, phenyl, or phenyl-alkyl group,
$R_2$ designates a hydrogen atom or an optionally substituted alkyl group, or, $R_1$ and $R_2$ taken together with the adjacent nitrogen atom represent a saturated heterocyclic ring,
$R_3$ is a hydrogen atom or an optionally substituted alkyl group,
Z is $-NH_2$; which comprises contacting a compound, selected from oxamide or its diacetyl derivative, of formula (II)

$$R_4HN-\underset{\underset{O}{\|}}{C}-\underset{\underset{O}{\|}}{C}-NHR_4 \qquad (II)$$

wherein
$R_4$ is a hydrogen atom or an acetyl group, with a hydrazine derivative of formula (III)

$$R_1R_2N-NHR_3 \qquad (III)$$

wherein
$R_1$, $R_2$, and $R_3$ are as defined above.

2. The process of claim 1 wherein the reaction is carried out at a temperature of from room temperature to 100° C.

3. The process of claim 2 wherein the temperature is from 30 to 80° C.

4. The process of claim 1 wherein the hydrazine derivative is employed in an excess with respect to the reaction stoichiometry.

5. The process of claim 1 wherein the reaction between the oxamide derivative (II) and the hydrazine derivative (III) is carried out in the presence of water or of an inert, polar, organic solvent.

6. The process of claim 1 for the preparation of a compound of formula (I) wherein Z is as defined in claim 1 and $R_1$, $R_2$, and $R_3$ represent a hydrogen atom.

7. The process of claim 6 wherein hydrazine hydrate is employed as the hydrazine derivative (III).

8. The process of claim 6 wherein the oxamide derivative (II) is reacted with an excess of $NH_2-NH_2\cdot H_2O$, in the absence of a solvent or in the presence of water.

* * * * *

UNITED STATES PATENT AND TRADEMARK OFFICE
CERTIFICATE OF CORRECTION

PATENT NO. : 5,017,721

DATED : May 21, 1991

INVENTOR(S) : Giuseppe Messina et al.

It is certified that error appears in the above-identified patent and that said Letters Patent is hereby corrected as shown below:

Title page item (73):
    The Assignee information is incorrect, should be,

--Enichem ANIC S.p.A., Palermo, Italy--.

Signed and Sealed this

Fifteenth Day of December, 1992

Attest:

DOUGLAS B. COMER

*Attesting Officer*     Acting Commissioner of Patents and Trademarks

UNITED STATES PATENT AND TRADEMARK OFFICE
CERTIFICATE OF CORRECTION

PATENT NO. : 5,017,721
DATED : May 21, 1991
INVENTOR(S) : Messina et al.

It is certified that error appears in the above-identified patent and that said Letters Patent is hereby corrected as shown below:

Column 1, line 40, change "per se" to --*per se*--.

Column 2, line 43, change "polar, organic" to --polar organic--.

Column 3, line 51, change "allow" to --allowed--.

Column 4, line 5, change "for further" to --further for--.

Column 4, line 58, change "polar, organic" to --polar organic--.

Signed and Sealed this

Second Day of February, 1993

Attest:

STEPHEN G. KUNIN

Attesting Officer

Acting Commissioner of Patents and Trademarks